US00PP26546P2

(12) United States Plant Patent
O'Byrne

(10) Patent No.: US PP26,546 P2
(45) Date of Patent: Mar. 29, 2016

(54) BARBERRY PLANT NAMED 'O'BYRNE'

(50) Latin Name: *Berberis thunbergii*
Varietal Denomination: O'Byrne

(71) Applicant: Ernest O'Byrne, Eugene, OR (US)

(72) Inventor: Ernest O'Byrne, Eugene, OR (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 106 days.

(21) Appl. No.: 13/998,227

(22) Filed: Oct. 11, 2013

(51) Int. Cl.
*A01H 5/00* (2006.01)

(52) U.S. Cl.
USPC ..... Plt./241

(58) Field of Classification Search
USPC ..... Plt./241
See application file for complete search history.

*Primary Examiner* — Keith Robinson
(74) *Attorney, Agent, or Firm* — C. A. Whealy

(57) ABSTRACT

A new and distinct cultivar of Barberry plant named 'O'Byrne', characterized by its upright, outwardly arching and mounding plant habit; vigorous growth habit; freely branching habit; leaves that are dark red to orange red in color with narrow bright yellow green-colored margins; good garden performance; and resistance to Wheat Rust.

2 Drawing Sheets

Botanical designation: *Berberis thunbergii.*
Cultivar denomination: 'O'BYRNE'.

BACKGROUND OF THE INVENTION

The present invention relates to a new and distinct cultivar of Barberry plant, botanically known as *Berberis thunbergii* and hereinafter referred to by the name 'O'Byrne'.

The new Barberry plant is a product of a planned breeding program conducted by the Inventor in Eugene, Oreg. The new Barberry plant originated from a cross-pollination conducted by the Inventor during the spring of 2003 of Barberry *thunbergii* 'Aurea', not patented, as the female, or seed parent and Barberry *thunbergii* 'Rose Glow', not patented, as the male, or pollen, parent. The new Barberry plant was discovered and selected by the Inventor during the spring of 2004 as a single plant from within the progeny of the stated cross-pollination in a controlled environment in Eugene, Oreg.

Asexual reproduction of the new Barberry plant by softwood cuttings in a controlled greenhouse environment in Eugene, Oreg. since July, 2004 has shown that the unique features of this new Barberry plant are stable and reproduced true to type in successive generations of asexual reproduction.

SUMMARY OF THE INVENTION

Plants of the new Barberry have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'O'Byrne'. These characteristics in combination distinguish 'O'Byrne' as a new and distinct Barberry plant:

1. Upright, outwardly arching and mounding plant habit.
2. Vigorous growth habit.
3. Freely branching habit.
4. Leaves that are dark red to orange red in color with narrow bright yellow green-colored margins.

5. Good garden performance.
6. Resistance to Wheat Rust.

Plants of the new Barberry can be compared to plants of the female parent, 'Aurea'. Plants of the new Barberry differ primarily from plants of 'Aurea' in leaf color as leaves of plants of 'Aurea' are yellow green in color and do not have bright green-colored margins. In addition, plants of the new Barberry are more high light tolerant than plants of 'Aurea'.

Plants of the new Barberry can be compared to plants of the male parent, 'Rose Glow'. Plants of the new Barberry differ primarily from plants of 'Rose Glow' in leaf color as leaves of plants of 'Rose Glow' are pink and burgundy in color without bright green-colored margins.

Plants of the new Barberry can be compared to plants of the *Berberis thunbergii* 'Celeste', disclosed in U.S. Plant Pat. No. 24,586. In side-by-side comparisons conducted in Grand Haven, Mich., plants of the new Barberry differed primarily from plants of 'Celeste' in leaf color as leaves of plants of 'Celeste' were dark greyed purple to dark greyed orange in color without bright green-colored margins.

BRIEF DESCRIPTION OF THE PHOTOGRAPHS

The accompanying colored photographs illustrate the overall appearance of the new Barberry plant showing the colors as true as it is reasonably possible to obtain in colored reproductions of this type. Colors in the photographs may differ slightly from the color values cited in the detailed botanical description which accurately describe the colors of the new Barberry plant.

The photograph on the first sheet is a side perspective view of a typical plant of 'O'Byrne' grown in an outdoor nursery.

The photograph on the second sheet is a close-up view of a typical plant of 'O'Byrne'.

DETAILED BOTANICAL DESCRIPTION

The aforementioned photographs and following observations, measurements and values describe plants grown during the summer in ground beds in an outdoor nursery in Grand Haven, Mich. and under cultural practices which closely approximate commercial Barberry production. Plants used for the photographs and description were six years old. In the following detailed description, color references are made to The Royal Horticultural Society Colour Chart, 1995 Edition, except where general terms of ordinary dictionary significance are used.

Botanical classification: *Berberis thunbergii* 'O'Byrne'.

Parentage:

*Female, or seed, parent*.—Barberry *thunbergii* 'Aurea', not patented.

*Male, or pollen, parent*.—Barberry *thunbergii* 'Rose Glow', not patented.

Propagation:

*Type*.—By softwood cuttings.

*Time to initiate roots, summer*.—About one month at temperatures about 24° C.

*Time to produce a rooted young plant, summer*.—About eight months at temperatures about 24°.

*Root description*.—Fine to thick; somewhat fleshy and fibrous; brown and yellow in color.

*Rooting habit*.—Freely branching; dense.

Plant description:

*Plant form and growth habit*.—Perennial deciduous shrub; upright, outwardly arching and mounding plant habit; vigorous growth habit; freely branching habit with about 115 lateral branches developing per plant.

*Plant height*.—About 68 cm.

*Plant diameter* (*area of spread*).—About 72 cm.

Lateral branch description:

*Length*.—About 32 cm.

*Diameter*.—About 2 mm to 4 mm.

*Internode length*.—About 1 cm.

*Aspect*.—Erect to outwardly arching.

*Strength*.—Strong, flexible.

*Texture*.—Smooth, glabrous.

*Color*.—Close to 183A and 166A.

*Thorns*.—Quantity: One thorn developing at each node. Length: About 6 mm. Width at the base: About 2.5 mm. Color: Close to 34A, 53A or 138B depending on light level. Texture: Smooth, glabrous.

Leaf description:

*Arrangement*.—Opposite or whorled; simple.

*Length*.—About 2 cm.

*Width*.—About 1 cm.

*Shape*.—Elliptic.

*Apex*.—Mucronate.

*Base*.—Attenuate.

*Margin*.—Entire.

*Texture, upper and lower surfaces*.—Smooth, glabrous; flat; somewhat glossy.

*Venation pattern*.—Pinnate.

*Color*.—Developing leaves, upper surface: Close to 53B; under high light conditions, closer to 35A. Developing leaves, lower surface: Close to 53A; under high light conditions, closer to 34A. Fully expanded leaves, upper surface: Close to 53A; under high light conditions, closer to 34A; narrow margins, close to 154B; under low light conditions, closer to 138B; venation, close to 53A or 34A depending on light level. Fully expanded leaves, lower surface: Close to 53A; under high light conditions, closer to 34A; under low light conditions, closer to 138B; venation, close to 53A or 34A depending on light level.

*Petiole*.—Length: About 6 mm. Diameter: About 1 mm. Texture, upper and lower surfaces: Smooth, glabrous. Color, upper and lower surfaces: Close to 53A or 34A depending on light level.

Flower description:

*Flower arrangement and habit*.—Flowers arranged in terminal and axillary racemes; flowers face outwardly to drooping; freely flowering habit with about four to eight flowers per inflorescence.

*Fragrance*.—None detected.

*Natural flowering season*.—Plants of the new Barberry flower during April and May in Michigan.

*Flower longevity*.—Flowers last about two to four weeks on the plant; flowers not persistent.

*Inflorescence length*.—About 3.5 cm.

*Inflorescence diameter*.—About 2.5 cm.

*Flower diameter*.—About 7 mm.

*Flower length* (*height*).—About 5 mm.

*Flower buds*.—Length: About 3 mm. Diameter: About 3 mm. Shape: Rounded. Color: Close to 144A.

*Petals*.—Arrangement: Four to six petals in a single whorl. Length: About 5 mm. Width: About 4 cm. Shape: Elliptic to obovate. Apex: Obtuse. Margin: Entire. Texture, upper and lower surfaces: Smooth, glabrous. Color: When opening, upper and lower surfaces: Close to 4B. Fully opened, upper and lower surfaces: Close to 4B; color becoming closer to 4C with development.

*Sepals*.—Arrangement: Four to six sepals in a single whorl. Length: About 4 mm. Width: About 3 mm. Shape: Elliptical to obovate. Apex: Obtuse. Base: Cuneate to obtuse. Margin: Entire. Texture, upper and lower surfaces: Smooth; glabrous. Color: When developing, upper surface: Close to 4C. When developing, lower surface: Close to 4C flushed with close to 179B. Fully developed, upper surface: Close to 4C. Fully developed, lower surface: Close to 4C flushed with close to 179B.

*Peduncles*.—Length: About 1 cm. Diameter: About 1 mm. Aspect: About 30° from lateral branch axis. Strength: Strong; wiry, flexible. Texture: Smooth, glabrous. Color: Close to 144A.

*Pedicels*.—Length: About 6 mm. Diameter: About 1 mm. Aspect: About 30° to 45° from peduncle axis. Strength: Strong; wiry, flexible. Texture: Smooth, glabrous. Color: Close to 144A.

*Reproductive organs*.—Stamens: Quantity: Four per flower. Anther shape: Two-lobed. Anther length: About 0.5 mm. Anther color: Close to 4C. Pollen amount: Scarce. Pollen color: Close to 4C. Pistils: Quantity: One per flower. Pistil length: About 2 mm. Style length: About 2 mm. Style color: Close to 144A. Stigma color: Close to 144A. Ovary color: Close to 144A. Seeds and fruits: Seed and fruit development have not been observed on plants of the new Barberry.

Garden performance: Plants of the new Barberry have been observed to have excellent garden performance and to tolerate high light, rain, wind and temperatures ranging from about −30° C. to about 40° C.

Pathogen & pest resistance: Plants of the new Barberry have been observed to be resistant to Wheat Rust (*Puccinia* sp.). Plants of the new Barberry have not been shown to be resistant to pests and other pathogens common to Barberry plants.

It is claimed:

1. A new and distinct Barberry plant named 'O'Byrne' as illustrated and described.

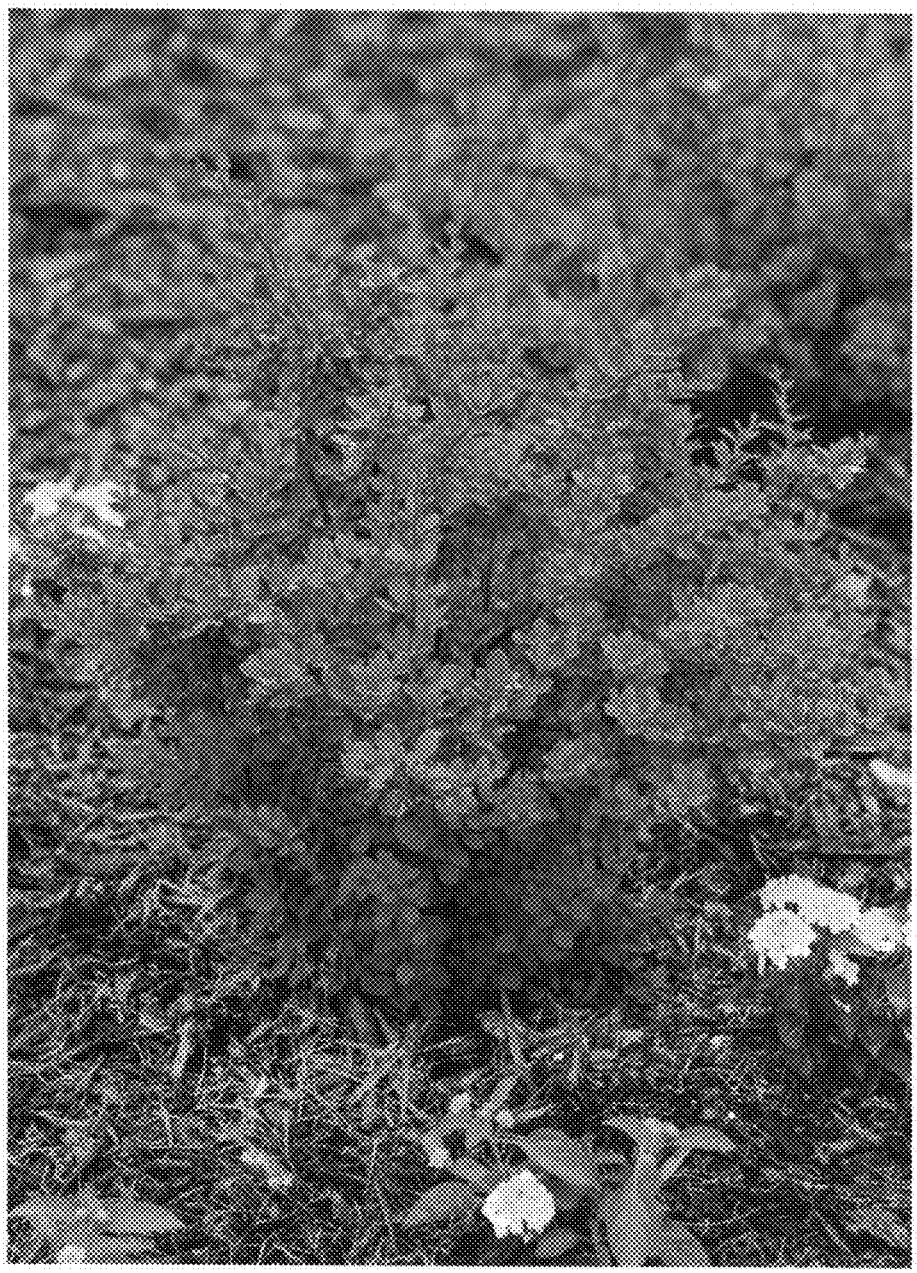

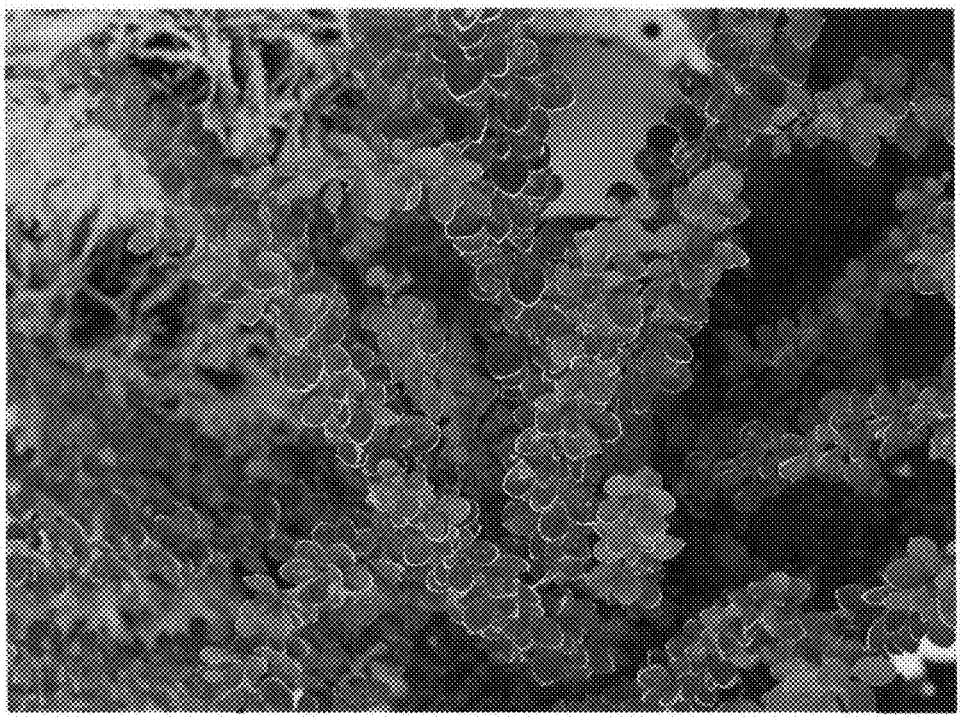

* * * * *